United States Patent [19]

Suzuki

[11] 3,989,726
[45] Nov. 2, 1976

[54] PLATINUM CATALYZED ISOMERIZATION OF ALKENYL SUCCINIC ANHYDRIDES
[75] Inventor: Shigeto Suzuki, San Francisco, Calif.
[73] Assignee: Chevron Research Company, San Francisco, Calif.
[22] Filed: Sept. 15, 1975
[21] Appl. No.: 613,599

[52] U.S. Cl. .................................. 260/346.8 R
[51] Int. Cl.$^2$ .................................. C07D 307/60
[58] Field of Search .......................... 260/346.8 R

[56] References Cited
UNITED STATES PATENTS
2,764,597   9/1956   Barney .......................... 260/346.3

Primary Examiner—Henry R. Jiles
Assistant Examiner—Bernard Dentz
Attorney, Agent, or Firm—G. F. Magdeburger; John Stoner, Jr.; W. Keith Turner

[57] ABSTRACT

A process for preparing alkyl maleic anhydrides which comprises heating a lower alkenyl succinic anhydride in the presence of a catalytic amount of a platinum salt in combination with a weakly basic material under conditions effective to isomerize the alkenyl succinic anhydride.

13 Claims, No Drawings

PLATINUM CATALYZED ISOMERIZATION OF ALKENYL SUCCINIC ANHYDRIDES

BACKGROUND OF THE INVENTION

This invention relates to the preparation of select alkyl maleic anhydrides from alkenyl succinic anhydrides. Alkyl maleic anhydrides prepared in accordance with this invention are useful intermediates in the preparation of alphaalkyl-beta-alkenyl succinic anhydrides which are known to be useful paper sizing agents and gasoline detergent additives.

A variety of processes for the preparation of alkenyl succinic anhydrides have been known and used for many years. For instance, U.S. Pat. No. 2,411,215, granted Nov. 16, 1946, and U.S. Pat. No. 3,819,660, granted June 25, 1974, describe the 1,2-addition reaction of monoolefins with maleic anhydride to prepare the corresponding alkenyl succinic anhydride. In general, the reaction process according to the reaction scheme:

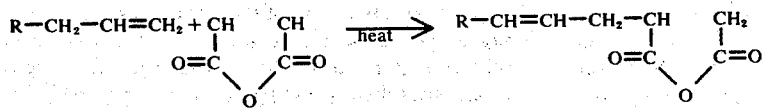

While alkenyl succinic anhydrides are useful products, there is a continuing need to develop a simple process for preparing alkyl maleic anhydrides. Toward this aim, it would be desirable to develop a means of isomerizing the alkenyl exocyclic double bond of alkenyl succinic anhydrides back into the anhydride ring to form alkyl maleic anhydrides.

The use of various acid catalysts to isomerize aliphatic alkenes is described in the prior art. For instance, Noller (Ed.), "Chemistry of Organic Compounds 3rd", W. B. Saunders (1966) describes the acid-catalyzed interconversion of 1-butene and cis- and trans-2-butene. Additionally, Noller discloses the thermally induced rearrangement of itaconic anhydride to citraconic anhydride.

SUMMARY OF THE INVENTION

The process of the present invention comprises heating a lower alkenyl succinic anhydride of the formula

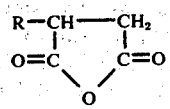

wherein R is an alkenyl group containing from about 3 to 7 carbon atoms, at a temperature below about 250° C in the presence of a catalytic amount of a platinum salt in combination with a weakly basic material.

DETAILED DESCRIPTION OF THE INVENTION

The present invention relates to the discovery that select alkyl maleic anhydrides can be prepared from corresponding alkenyl succinic anhydrides utilizing as a catalytic system from about 0.1% to 15.0%, by weight, of a platinum salt in combination with from about 0.5% to 15.0%, by weight of a weakly basic material.

The alkenyl succinic anhydrides suitable for use in the practice of this process can be obtained by a variety of well-known reactions. In general, alkenyl succinic anhydrides can be prepared by thermal condensation of maleic anhydrides with monoolefins. U.S. Pat. Nos. 2,411,215 and 3,819,660, previously mentioned, describe typical preparations.

More particularly, alkenyl succinic anhydrides suitable for use herein are characterized by an alkenyl substituent containing from about 3 to 7, preferably from about 3 to 5, carbon atoms. It has been found that the higher-chain-length alkenyl succinic anhydrides, containing greater than about 7 carbon atoms in the alkenyl group, when heated in the presence of an isomerization catalyst, predominantly yield the akenyl succinic anhydride isomers and only minor amounts of the desired maleic anhydride isomer. Accordingly, alkenyl succinic anhydrides having greater than about 7 carbon atoms in the alkenyl substituent are unsatisfactory for use herein.

Illustrative suitable alkenyl succinic anhydrides include, for example, allyl succinic anhydride, butenyl succinic anhydride, hexenyl succinic anhydride, heptenyl succinic anhydride, 4,4-dimethyl pentenyl succinic anhydride, 3,4-dimethyl pentenyl succinic anhydride, and the like. The position of the alkenyl double bond is not critical to the isomerization; however, as the double bond is positioned farther than the 2,3 position from the anhydride ring the process will produce a mixture of products in which the double bond is predominantly in the exocyclic positions thereby reducing the conversion to alkyl maleic anhydride. Accordingly, alkenyl succinic anhydrides, such as allyl succinic anhydride, having the double bond in the 1,2 or 2,3 position are preferred.

It has been found that only select Group VIII noble transition metal systems will efficiently catalyze the desired isomerization. The present process relates to the isomerization of alkenyl succinic anhydrides in the presence of catalytic amounts of a platinum salt in combination with a weakly basic material.

The amount of platinum salt and the amount of base present in the system can vary over a wide range. For example, amounts of each component ranging from about 0.1% to about 15.0%, by weight of alkenyl succinic anhydride, are satisfactory, and amounts ranging from about 1.0% to about 5.0% are preferred. In general, the platinum salt is used at the lower levels of concentration, whereas the basic materials are used at the higher levels of concentration.

Suitable platinum salts include, for example, alkali metla platinum halide salts of the formula

wherein L is alkali metal such as sodium, potassium, or magnesium; X is halide such as chloride, bromide, or iodide; n is 0 to 5; m is 0 to 3; and m+n is 3 to 6. It is understood, of course, that m+n represents the corrdination number of platinum, i.e., three-, four-, five- or six-coordinate, and that m represents the valence or oxidation state of the platinum moiety. Additionally, the platinum salts depicted represent only the empirical composition which may exist in a dimeric or polymeric form.

Illustrative platinum salts suitable for use herein include palladium halides such as $K_2PtCl_4$, $NaPtCl_5$, $k_2PtBr_4$ and $Mg_2PdI_4$.

The preferred platinum salt is dipotassium platinum tetrachloride.

It has been found that, when used alone, the abovedescribed platinum salts isomerize the alkenyl double bond of most alkenyl succinic anhydrides one step only. Accordingly, the platinum salt is utilized in combination with a weakly basic material to promote isomerization. Promoting basic materials suitable for use in combination with the platinum salt include both soluble and insoluble organic and inorganic bases having a $pK_b$ of from 2 to about 10.

Suitable soluble bases include, for example, organic tertiary amines and phosphines. A thorough discussion of organic amines and phosphines is found at Chapter 24 of Noller's "Chemistry of Organic Compounds 3rd". Illustrative suitable organic tertiary amines include alkyl amines such as trimethylamine, methylethyl-i-propylamine and tributylamine; and aromatic amines such as N,N-dimethyl toluidine, N,N-dimethylaniline, and methyl diphenylamine. Illustrative suitable phosphines include phenyl dimethylphiosphine, diphenyl methylphosphine, triphenylphosphine, tributylphosphine, tripropylphosphine, methylethylpropylphosphene, and the like.

Suitable insoluble bases include, for example, the basic ion exchange resins such as polypropylene-vinylpyridine graft copolymers, aminated divinylbenzene-vinylbenzyl chloride copolymers, and the like.

It is apparent that the choice of base is not limited to specific materials; however, it has been found that dimethylaniline and triphenylphosphine are particularly well suited for combination with the platinum salts.

The isomerization process of the invention is conducted in a fluid phase, i.e., either gaseous or liquid phase, in the presence or in the absence of an inert diluent. The process is carried out by either sequentially or simultaneously contacting the alkenyl succinic anhydride with the platinum salt and basic material, depending upon the selection of either a soluble or insoluble base. It has been found that when soluble bases are employed it is preferable to add the base after the initial isomerization has been effected using the platinum salt; otherwise these bases somewhat deactivate the platinum salt and isomerization is slowed. On the other hand, insoluble bases may be added initially without deactivating the platinum salt.

Although isomerization will proceed at moderate temperatures and pressures, for most practical applications reaction temperatures ranging from about 80° C to about 250° C are satisfactory, and temperatures of from about 100° C to about 230° C are preferred. Within this temperature range, reaction time will vary from a few minutes to a few hours. The process is conducted at or above atmospheric pressure; pressures from about 1 atmosphere to 200 atmospheres are satisfactory.

At the conclusion of isomerization, equilibrium is reached between the various exocyclic alkenyl succinic anhydrides and alkyl maleic anhydride. Alkyl maleic anhydride can be recovered by conventional means such as distillation, and the alkenyl succinic anhydrides are suitably recycled for further isomerization.

A principal advantage of the present process resides in the relatively high yield of alkyl maleic anhydride isomer obtained at equilibrium. While yields will vary depending upon such factors as the choice of starting material, catalyst, and temperature of reaction, it has been found that yields on the order of at least about 40%, by weight of alkyl maleic anhydride are typical.

Another advantage of the present process for preparing alkyl maleic anhydrides is that a second olefinic moiety may be added to the unsubstituted ring carbon atom, thereby providing a simple synthetic route to alpha-alkyl-beta-alkenyl succinic anhydrides, useful as detergent and paper-sizing compounds. The over-all reaction process typically proceeds according to the scheme:

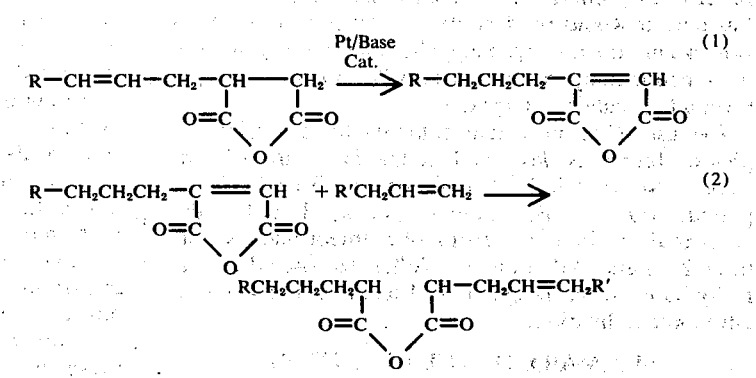

Although schematically presented as a two-step reaction in practice alpha-alkyl-beta alkenyl succinic anhydrides can be prepared in accordance with thiis invention by heating at a temperature below about 250° C a mixture comprising an alkenyl succinic anhydride and an olefin, in the presence of a catalytic amount of a platinum salt in combination with a basic material, as described above. This process is believed to kinetically favor isomerization to form the intermediate maleic anhydride, thereby providing high yields of desired product.

In the above process, the second olefin molecule may be of any chain length; however, in many applications olefins containing an average of at least 8 carbon atoms are preferred.

EXAMPLES

The following examples illustrate the practice of this invention, but are not intended to be limiting thereof.

EXAMPLE I — Isomerization of Allyl Succinic Anhydride Using k₂PtCl./Soluble Base 2.0 g of allyl succinic anhydride were placed in a reaction vessel. 0.03 g of disodium platinum tetrachloride (1.5% by weight based on anhydride) were added with constant stirring. The reaction mixture was heated to a temperature of 100° C for 90 minutes, and then to a temperature of 150° C for 30 minutes.

0.05 g of triphenylphosphine (2.5% by weight based on anhydride) were added. The reaction was allowed to proceed 90 additional minutes at 150° C, at which time analytical analysis confirmed a product distribution of 26.0% propyl maleic anhydride and the balance propenyl succinic anhydrides and unknown.

Another 0.05 g aliquot of triphenylphosphine was added. The reaction mixture was heated to 200° C for 60 minutes; at which time analytic analysis confirmed a product distribution of 29.2 propyl maleic anhydride the balance propenyl succinic anhydrides and unknown.

An equivalent amount of butenyl succinic anhydride, hexenyl succinic anhydride, heptenyl succinic anhydride, 4,4-dimethyl pentenyl succinic anhydride and 3,4-dimethyl propenyl succinic anhydride, respectively, is substituted for allyl succinic anhydride and isomerized in a like fashion.

An equivalent amount of dipotassium platinum tetrabromide, dipotassium platinum tetraiodide, and dimagnesium platinum tetrachloride, respectively, is substituted for disodium platinum tetrachloride in the above procedure and substantially equivalent results are achieved.

An equivalent amount of trimethylamine, phenylenediamine and toluidine, respectively, is substituted for triphenylphosphine in the above procedure and substantially equivalent results are achieved.

EXAMPLE II -- Preparation of alpha-Alkylbeta-Alkenyl Succinic Anhydrides 1.30 g of alyl succinic anhydride, 2.25 g of 1-octene and 0.025 g of hydroquinone are placed in a sealed reaction vessel. 0.015 g dipotassium platinum tetrachloride and 0.2 g of a graft copolymer of polypropylene and vinylpyridine are added. The reaction mixture is heated to a temperature of 230° C, and allowed to proceed for 24 hours. Analyses of the reaction product by gas chromatography shows substantial conversion of initially added allyl succinic anhydride to alpha-propyl-beta-octenyl succinic anhydride.

A duplicate run without the added dipotassium platinum tetrachloride and graft copolymer of polypropylene and vinyl pyridine gave hardly any reaction.

What is claimed is:

1. A process for preparing alkyl maleic anhydrides which comprises heating an alkenyl succinic anhydride of the formula $$R-C-CH_2$$
$$O=C\quad C=O$$
$$\diagdown O \diagup$$

wherein R is alkenyl containing 3 to 7 carbon atoms, at a temperature below about 250° C in the presence of a catalytic amount of an alkali metal platinum halide salt in combination with a weakly basic material having a $pK_b$ of from 2 to about 10.

2. A process according to claim 1 wherein said process is conducted at a temperature in the range from about 80° C to about 250° C.

3. A process according to claim 1 wherein said succinic anhydride is allyl succinic anhydride.

4. A process according to claim 1 wherein said alkali metal platinum halide is dipotassium platinum tetrahalide.

5. A process according to claim 1 wherein said base is soluble.

6. A process according to claim 5 wherein said soluble basic material is an organic tertiary amine.

7. A process according to claim 6 wherein said amine is dimethylaniline.

8. A process according to claim 5 wherein said soluble basic material is an organic phosphine.

9. A process according to claim 8 wherein said phosphine is triphenylphosphine.

10. A process according to claim 1 wherein said base is insoluble.

11. A process according to claim 10 wherein said base is a basic ion-exchange resin.

12. A process according to claim 11 wherein said insoluble basic material is polypropylene-vinylpyridine graft copolymer.

13. A process for preparing alpha-alkyl-beta-alkenyl succinic anhydrides which comprises heating a mixture comprising an alkenyl succinic anhydride of the formula $$R-CH-CH_2$$
$$O=C\quad C=O$$
$$\diagdown O \diagup$$

wherein R is alkenyl containing 3 to 7 carbon atoms, and an olefin to a temperature below about 250° C in the presence of a catalytic amount of an alkali metal platinum halide in combination with a weakly basic material having a $pK_b$ of from 2 to about 10.

* * * * *

UNITED STATES PATENT AND TRADEMARK OFFICE
CERTIFICATE OF CORRECTION

PATENT NO. : 3,989,726
DATED : November 2, 1976
INVENTOR(S) : Shigeto Suzuki

It is certified that error appears in the above-identified patent and that said Letters Patent are hereby corrected as shown below:

Col. 6, line 5, Claim 1, "$R-\underset{|}{C}-\underset{|}{C}H_2$" should read $--R-\underset{|}{C}H-\underset{|}{C}H_2--$

Signed and Sealed this

Twenty-second Day of February 1977

[SEAL]

Attest:

RUTH C. MASON
*Attesting Officer*

C. MARSHALL DANN
*Commissioner of Patents and Trademarks*